(12) United States Patent
Zinn

(10) Patent No.: US 9,364,289 B2
(45) Date of Patent: Jun. 14, 2016

(54) INTERLEAVED MANIPULATOR

(71) Applicant: Wisconsin Alumni Research Foundation, Madison, WI (US)

(72) Inventor: Michael Zinn, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 310 days.

(21) Appl. No.: 14/049,511

(22) Filed: Oct. 9, 2013

(65) Prior Publication Data

US 2015/0100065 A1 Apr. 9, 2015

(51) Int. Cl.
*G06F 19/00* (2011.01)
*A61B 19/00* (2006.01)

(52) U.S. Cl.
CPC ..... *A61B 19/2203* (2013.01); *A61B 2019/2242* (2013.01)

(58) Field of Classification Search
CPC ........... A61B 17/1725; A61B 17/7266; A61B 17/7208; A61B 2019/301; A61B 19/2203
USPC ............. 700/245; 600/481, 485, 490; 606/64, 606/130
See application file for complete search history.

(56) References Cited

U.S. PATENT DOCUMENTS

| | | | |
|---|---|---|---|
| 8,083,667 B2 * | 12/2011 | Cooper | A61B 1/00087 600/104 |
| 9,039,685 B2 * | 5/2015 | Larkin | A61B 19/2203 606/15 |
| 2009/0312755 A1 | 12/2009 | Thapliyal et al. | |
| 2010/0082041 A1 * | 4/2010 | Prisco | A61B 19/2203 606/130 |
| 2011/0071508 A1 * | 3/2011 | Duval | A61B 1/00087 606/1 |
| 2012/0078053 A1 * | 3/2012 | Phee | A61B 1/00147 600/139 |
| 2014/0142377 A1 * | 5/2014 | Yang | A61B 1/0055 600/104 |
| 2015/0157191 A1 * | 6/2015 | Phee | A61B 1/00133 600/106 |
| 2015/0230697 A1 * | 8/2015 | Phee | A61B 1/0125 600/106 |

OTHER PUBLICATIONS

Mack, Minimally Invasive and RoboticSurgery, Internet, 2001, p. 568-572.*
W. T. Townsend, "The effect of transmission design on force-controlled manipulator performance," Ph.D. Ph.D., Dept. of Mechanical Engineering, Massachusetts Institute of Technology, Cambridge, MA, 1988.
W. T. Townsend and J. K. Salisbury, "Mechanical bandwidth as a guideline to high-performance manipulator design," in Robotics and Automation, 1989. Proceedings., 1989 IEEE International Conference on, 1989, pp. 1390-1395 vol. 1393.
(Continued)

*Primary Examiner* — McDieunel Marc
(74) *Attorney, Agent, or Firm* — Crawford Maunu PLLC

(57) ABSTRACT

Various apparatuses and methods involve flexible components for insertion into tissue, such as for minimally-invasive surgical procedures. As consistent with one or more embodiments, an apparatus includes a plurality of elongated flexible segments and one or more rigid actuators coupled between the flexible segments. One or more tendons extend within and moves the flexible segments, which elastically flex upon insertion into tissue. Each rigid actuator also operates to move one or more of the flexible segments, providing further movement control. A manipulator circuit is coupled to each rigid actuator and operates to position one or more of the segments by actuating the rigid actuator (e.g., via electrical and/or mechanical input).

20 Claims, 7 Drawing Sheets

(56) References Cited

OTHER PUBLICATIONS

K. Ogata, "Describing-Function Analysis of Nonlinear Control Systems," in Modern Control Engineering, 2 ed Englewood Cliffs, New Jersey, USA: Prentice-Hall, 1990, pp. 645-676.

F. Arai, M. Ito, T. Fukuda, M. Negoro, and T. Naito, "Intelligent assistance in operation of active catheter for minimum invasive surgery," in RO-MAN '94 Nagoya, Proceedings., 3rd IEEE International Workshop on Robot and Human Communication, 1994, pp. 192-197.

H. Choset and W. Henning, "A follow-the-leader approach to serpentine robot motion planning," ASCE Journal of Aerospace Engineering, vol. 12, pp. 65-73, 1999.

S. J. Schroeck, W. C. Messner, and R. J. McNab, "On compensator design for linear time-invariant dual-input single-output systems," Mechatronics, IEEE/ASME Transactions on, vol. 6, pp. 50-57, 2001.

Y. Bailly, A. Chauvin, and Y. Amirat, "Control of a high dexterity micro-robot based catheter for aortic aneurysm treatment," in Robotics, Automation and Mechatronics, 2004 IEEE Conference on, 2004, pp. 65-70.

M. Zinn, "A New Actuation Approach for Human Friendly Robotic Manipulation," Ph.D. Ph.D. Dissertation, Mechanical Engineering, Ph.D. thesis, Stanford University, Stanford, 2005. (Abstract only).

X. Kai and N. Simaan, "Actuation compensation for flexible surgical snake-like robots with redundant remote actuation," in Robotics and Automation (ICRA), Proceedings IEEE International Conference on, 2006, pp. 4148-4154.

A. Degani, H. Choset, A. Wolf, and M. A. Zenati, "Highly articulated robotic probe for minimally invasive surgery," in Robotics and Automation (ICRA), Proceedings IEEE International Conference on, 2006, pp. 4167-4172.

A. Degani, H. Choset, A. Wolf, T. Ota, and M. A. Zenati, "Percutaneous Intrapericardial Interventions Using a Highly Articulated Robotic Probe," in Biomedical Robotics and Biomechatronics (BioRob), The First IEEE/RAS-EMBS International Conference on, 2006, pp. 7-12.

M. W. Spong, S. Hutchinson, and M. Vidyasagar, Robot modeling and control: John Wiley & Sons Hoboken, NJ, 2006. (Book).

T. King, "Catheter Control System System Requirements Specification (Hansen Medical, Inc)," ed. Mountain View, CA, 2006. 25 (Copy Unavailable).

V. K. Chitrakaran, A. Behal, D. M. Dawson, and I. D. Walker, "Setpoint regulation of continuum robots using a fixed camera," Robotica, vol. 25, pp. 581-586, 2007.

D. B. Camarillo, C. F. Milne, C. R. Carlson, M. R. Zinn, and J. K. Salisbury, "Mechanics Modeling of Tendon-Driven Continuum Manipulators," Robotics, IEEE Transactions on, vol. 24, pp. 1262-1273, 2008.

M. Zinn, O. Khatib, B. Roth, and J. K. Salisbury, "Large Workspace Haptic Devices—A New Actuation Approach," in Symposium on Haptic Interfaces for Virtual Environment and Teleoperator Systems, 2008, pp. 185-192.

X. Kai and N. Simaan, "An Investigation of the Intrinsic Force Sensing Capabilities of Continuum Robots," Robotics, IEEE Transactions on, vol. 24, pp. 576-587, 2008.

J. Jayender, M. Azizian, and R. V. Patel, "Autonomous Image-Guided Robot-Assisted Active Catheter Insertion," Robotics, IEEE Transactions on, vol. 24, pp. 858-871, 2008.

J. Jayender, R. V. Patel, and S. Nikumb, "Robot-assisted Active Catheter Insertion: Algorithms and Experiments," The International Journal of Robotics Research, vol. 28, pp. 1101-1117, Sep. 1, 2009.

R. Webster, J. Swensen, J. Romano, and N. Cowan, "Closed-Form Differential Kinematics for Concentric-Tube Continuum Robots with Application to Visual Servoing," in Experimental Robotics. vol. 54, O. Khatib, V. Kumar, and G. Pappas, Eds., ed: Springer Berlin / Heidelberg, 2009, pp. 485-494.

R. J. Webster, J. M. Romano, and N. J. Cowan, "Mechanics of Precurved-Tube Continuum Robots," Robotics, IEEE Transactions on, vol. 25, pp. 67-78, 2009.

S. G. Yuen, D. T. Kettler, P. M. Novotny, R. D. Plowes, and R. D. Howe, "Robotic Motion Compensation for Beating Heart Intracardiac Surgery," The International Journal of Robotics Research, pp. 1355-1372, 2009.

D. B. Camarillo, C. R. Carlson, and J. K. Salisbury, "Configuration tracking for continuum manipulators with coupled tendon drive," IEEE Transactions on Robotics, vol. 25, pp. 798-808, 2009.

V. Reddy, P. Neuzil, P. Ricard, B. Schmidt, D. Shah, P. Jais, J. Kautzner, A. Natale, G. Hindricks, C. Herrera, Y. Vanekov, H. Lambert, and K.-H. Kuck, "Catheter Contact Force During Ablation of Atrial Flutter and Atrial Fibrillation: Results From the Toccata Multi-Center Clinical Study," Circulation, vol. 120, pp. 5705-5706, 2009.

P. E. Dupont, J. Lock, B. Itkowitz, and E. Butler, "Design and Control of Concentric-Tube Robots," Robotics, IEEE Transactions on, vol. 26, pp. 209-225 (2010).

R. S. Penning, J. Jung, J. A. Borgstadt, N. J. Ferrier, and M. R. Zinn, "Towards closed loop control of a continuum robotic manipulator for medical applications," in Robotics and Automation (ICRA), IEEE International Conference on, 2011, pp. 4822-4827.

J. Jung, R. S. Penning, N. J. Ferrier, and M. R. Zinn, "A Modeling Approach for Continuum Robotic Manipulators: Effects of Nonlinear Internal Device Friction," presented at the 2011 IEEE/RSJ International Conference on Intelligent Robots and Systems (IROS), San Francisco, 2011.

M. Mahvash and P. E. Dupont, "Stiffness Control of Surgical Continuum Manipulators," Robotics, IEEE Transactions on, vol. 27, pp. 334-345, 2011.

R. Penning, J. Jung, N. Ferrier, and M. Zinn, "An Evaluation of Closed-Loop Control Options for Continuum Manipulators," presented at the IEEE International Conference on Robotics and Automation, Saint Paul, Minnesota, USA, 2012.

A. Bajo and N. Simaan, "Kinematics-Based Detection and Localization of Contacts Along Multisegment Continuum Robots," Robotics, IEEE Transactions on, vol. 28, pp. 291-302, 2012.

W. Wei and N. Simaan, "Modeling, Force Sensing, and Control of Flexible Cannulas for Microstent Delivery," Journal of Dynamic Systems, Measurement, and Control, vol. 134, p. 041004, 2012.

B. L. Conrad, J. Jung, R. S. Penning, and M. R. Zinn, "Interleaved Continuum-Rigid Manipulation: An Augmented Approach for Robotic Minimally-Invasive Flexible Catheter-based Procedures," in Robotics and Automation (ICRA), Proceedings IEEE International Conference on, Karlsruhe, Germany, 2013.

\* cited by examiner

INTERLEAVED MANIPULATOR

FIELD

Aspects of various embodiments are directed to interleaved manipulator apparatuses and methods.

BACKGROUND

A variety of minimally-invasive surgical (MIS) systems, such as robotic systems, have been used for many different applications. For instance, many MIS manipulation based systems can be classified as either rigid-link manipulators, such as the Da Vinci system available from Intuitive Surgical of Sunnyvale, Calif. Other MIS manipulation based systems are classified as flexible continuum manipulators, such as the Artisan Extend catheter system available from Hansen Medical of Mountain View, Calif., or the Niboe ES system available from Stereotaxis of St. Louis, Mo.

While rigid-link manipulators have been used for a variety of applications, rigid components can introduce safety issues with regard to a variety of applications. On the other hand, flexible manipulators can provide desirable safety characteristics as compared to rigid manipulators, as a compliant structure combined with soft construction can be less likely to cause damage when contacting tissue. For these reasons, flexible manipulators such as flexible catheters have become the dominant interventional tool in applications where safety is of particular concern, such as vascular and intracardiac interventional procedures.

While MIS systems based on flexible manipulators have met with success, the very features that enable their safety characteristics can hinder their use in high performance manipulation tasks. Their soft compliant structure, in combination with internal friction, can result in poor position and force regulation and has limited their use to simpler surgical procedures. These and other matters have presented challenges to the implementation of MIS type apparatuses, systems and methods, for a variety of applications.

SUMMARY

Various example embodiments are directed to interleaved manipulators and their implementation.

According to an example embodiment, an apparatus includes a plurality of flexible segments, each segment having an outer wall that extends between respective ends of the segment, in which the outer wall elastically flexes upon the application of force to the outer wall, and in which the segments are coupled end-to-end from a proximal segment to a distal segment. One or more rigid actuators are coupled between the flexible segments and actuate/move one or more of the flexible segments relative to another one of the flexible segments. A tendon extends within the flexible segments, is coupled to the distal segment (e.g., at an end thereof) and manipulates at least one of the segments in response to movement of the tendon through the proximal segment or segments (e.g., by sliding through and/or twisting within the segments). A manipulator circuit is coupled to at least a first one of the actuators and positions at least one of the segments coupled to the first actuator by actuating the first actuator, such as by providing an electrical or mechanical input to the actuator.

Another embodiment is directed to a surgical apparatus having elongated segments coupled end-to-end via one or more interleaved, rigid actuators, as well as a tool at a distal end of the segments. A tendon extends into and/or through one or more of the segments, and is coupled to manipulate one or more of the segments as the tendon is moved (e.g., by moving the distal segment via control of a portion of the tendon extending out of a proximal segment). The elongated segments elastically flex during insertion into tissue, and the rigid actuator operates to move one or more of the segments. The tool interacts with the tissue via the distal segment, as directed by movement of the rigid actuator and the tendon. In some embodiments, the apparatus includes an actuator circuit that is electrically coupled to the rigid actuator and moves the segments relative to one another via the rigid actuator. In a further embodiment, a feedback circuit generates a feedback signal indicative of a position of one of the plurality of segments, and the actuator circuit controls movement of the rigid actuator in response to the feedback signal. In some implementations, the actuator circuit includes an electric motor that is connected to and drives a mechanical component of the rigid actuator. The electric motor may be located locally to the rigid actuator, or mechanically coupled remotely (e.g., via a shaft).

Another embodiment is directed to a method as follows. A manipulator is inserted into tissue of a patient, in which the manipulator includes a plurality of flexible segments, at least one rigid actuator coupled between two of the flexible segments and a tendon extending within the flexible segments. Each segment has an outer wall that extends between respective ends of the segment, and that elastically flexes upon the application of force to the outer wall as it is inserted into the tissue. The segments are coupled end-to-end and include at least a proximal segment and a distal segment. The distal segment is positioned by moving the tendon via the proximal end and controlling the rigid actuator to actuate and move one of the flexible segments relative to another one of the flexible segments. In some implementations, the rigid actuator is controlled in response to feedback indicative of a positional characteristic of the distal segment.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which.

Figure 1:
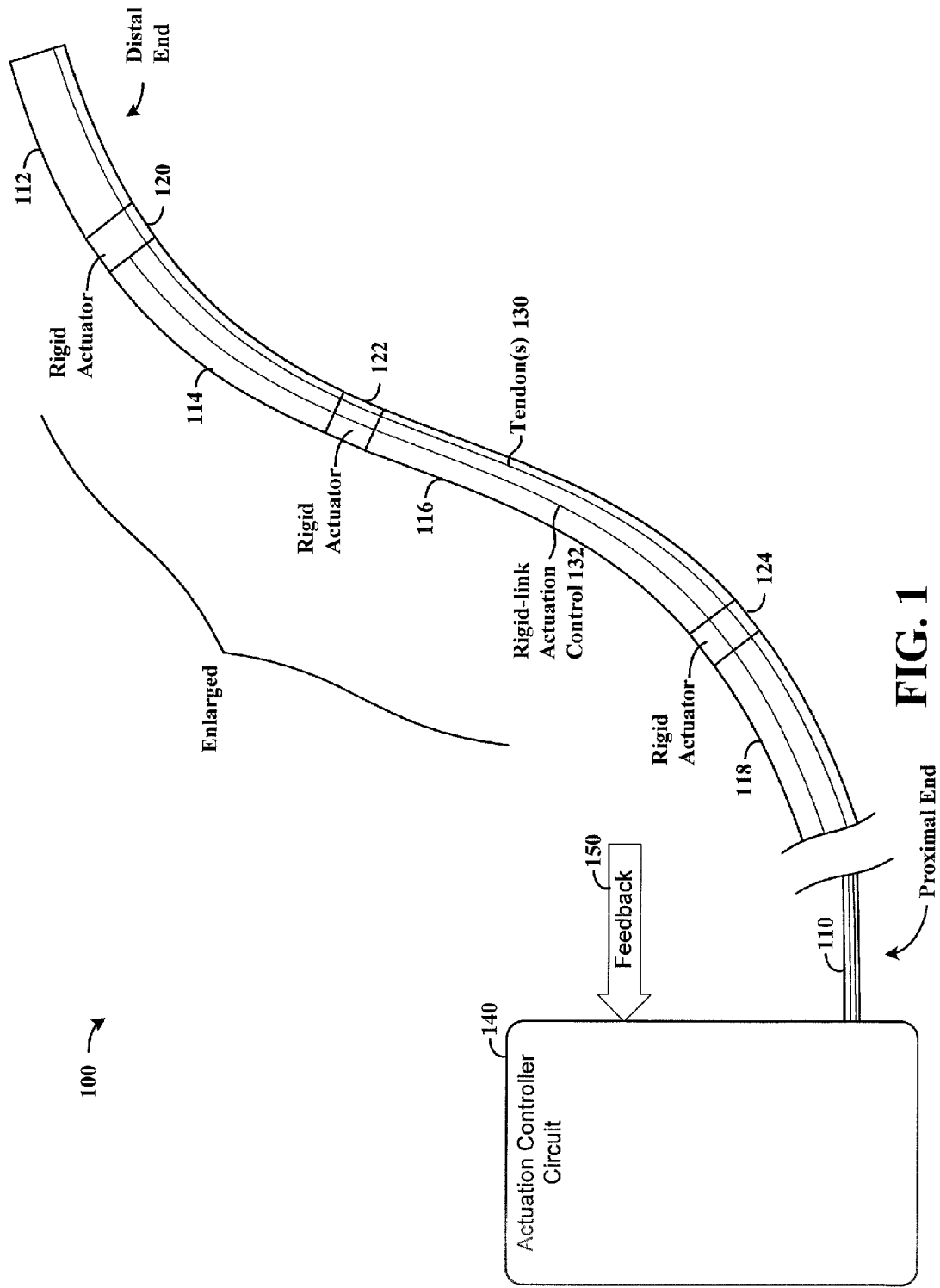
FIG. 1 shows a manipulator apparatus with interleaved flexible and rigid components, in accordance with an example embodiment of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is by way of illustration.

DETAILED DESCRIPTION

Aspects of the present disclosure are believed to be applicable to a variety of different types of apparatuses, systems and methods involving surgical devices, including devices often referred to as minimally invasive surgical devices. While not necessarily so limited, various aspects may be appreciated through a discussion of examples using this context.

Various example embodiments are directed to an interleaved continuum-rigid manipulator, which includes both flexible, actively actuated continuum segments and small, limited stroke rigid-link actuators. The small rigid-link joints are interleaved between successive continuum segments and provide respective motion capabilities. For instance, the rigid-link joints may provide redundant motion capability that is highly-controllable and enhances a motion capability provided by the continuum segments. The continuum segments provide larger-scale flexibility that is desirable for safety, with manipulation control being enhanced by the rigid-link joints. Such manipulators may be useful for a variety of applications, including the minimally invasive procedures discussed above, such as for valve replacement, stem cell injection, ablation, and atrial fibrillation.

In various embodiments, the active continuum segments provide large motion capability through a combination of tendon-driven articulation and telescoping motion, and have a compliant construction that enhances safety. The rigid-link joints employ both joint and limited stroke-actuators, with the joints being of relatively small size. In some instances, the joints are embedded inside the compliant segments. In connection with these embodiments, it has been discovered that by employing limited stroke actuation, the rigid-link joints can be implemented in a compact form that may be incorporated within the compliant segments. It has been further discovered that by combining this limited stroke actuation with the larger motion capability of the active continuum segments, a wide range of motion can be safely achieved while facilitating fine motor control for manipulation. Accordingly, the manipulators as described herein can be implemented with a wide variety of micro-scale applications.

In some embodiments, the actuators are used to facilitate active correction of motion errors. For instance, feedback regarding the position of the manipulator can be used to control the actuators to compensate for inaccurate movement of the compliant segments. Such an approach can, for example, facilitate the accurate placement of a tool or other component deployed by the manipulator, once the manipulator is in place. Such an approach may also be used to control movement of the manipulator as it is maneuvered in a patient. In these and other various contexts, small rigid-link joints can be implemented to linearize systems having overall behavior that is otherwise highly nonlinear, facilitating effective use of feedback control to enhance performance.

Various embodiments are directed to a robotic apparatus having a manipulator as discussed above and an automated robotic control circuit that controls the manipulator. In one such example, an interleaved manipulator is implemented with a plurality of compliant segments interleaved with rigid-link joints as discussed herein. A robotic control circuit is communicatively coupled to actuate the rigid-link joints as the manipulator is inserted into and/or after the manipulator has been placed in a patient. In some implementations, the control circuit also controls manipulation of the compliant sections, such as via tendons and telescoping components.

In some embodiments, the robotic apparatus further includes one or more feedback components, such as a feedback circuit, which provides feedback indicative of a position of the manipulator. Such feedback may include, for example, position sensors that sense the relative position of the manipulator, such as when deploying and maneuvering the manipulator within a patient, or for positioning a tool that interacts with tissue in the patient. When compliant segment manipulation fails to place the manipulator or a tool deployed by the manipulator in a proper position, feedback from a position sensor is used to detect any misplacement and is used to precisely maneuver the manipulator into the proper position using the rigid-link joints. Other feedback may include pressure or other sensors indicating an interaction with the patient's tissue, such as when the manipulator is maneuvered within the patient or when a tool is engaged with the patient. Another type of feedback that may be used with one or more embodiments is obtained via an imaging sensor that provides an image of the position of the manipulator (or a tool deployed by the manipulator), within a patient. The image is used to identify a position of the sensor, and when the position is incorrect, one or more of the rigid-link joints are manipulated to correct the position.

The rigid-link joints are actuated using local and/or remote actuators, in accordance with various embodiments. For instance, some embodiments employ actuators embedded within or adjacent to rigid-link joints. Such actuators may include, for example, piezoelectric actuators, micro electrical mechanical systems (MEMS) actuators, and others suitable for embedded medical devices (e.g., employing actuators or actuator components available from New Scale Technologies of Victor N.Y., such as the Squiggle micro motor). Such actuators may be implemented with high output impedance, which can help overcome limitations relating to limited output torque (or force).

The type of rigid-link joints may be tailored to suit particular applications. In some embodiments, limited joint stroke actuators are used to facilitate compact rigid joints, such as for correcting flexible segment motion errors with otherwise limited movement at the rigid joints. Various such embodiments involve overlapping motion control between flexible segments and rigid joints, with the rigid joints being implemented to correct motion errors in the flexible segments. In other implementations, relatively large-motion joints are used to provide enhanced dexterity, such as to provide articulation about acute angles, or to provide articulation to conform to complex tissue such as by providing articulation about multiple acute angles via respective rigid actuators coupled by flexible segments.

Various joint actuation approaches are implemented to suit respective embodiments. For example, certain embodiments employ revolute joints driven by the linear piezoelectric actuators described. Where the limited force density of the piezoelectric actuator is insufficient, gear reduction, accompanied by a repeating mechanism such as a ratchet, is used to maintain a large motion stroke while attaining the higher output forces or torques that cannot be achieved with the actuator alone. Other embodiments are directed to addressing closed-loop bandwidth matters in regard to controlling actuation. Certain embodiments involve using local control, such as with an actuator located at rigid-link joints and/or in other locations near the rigid-link joints. Moreover, flexible segments are also locally actuated in accordance with one or more embodiments here, such as by controlling a tendon with an actuator located within or nearby the flexible segment being actuated. Such approaches can be implemented to reduce/minimize drive train compliance and the deleterious effect of drive train flexible modes, thus helping to achieve higher rigid-link joint closed-loop bandwidths with associated performance improvements.

Another example embodiment is directed to an apparatus having a plurality of flexible segments coupled end-to-end, with each segment having an outer wall that extends between respective ends of the segment, and with one or more rigid actuators coupling the ends of the two or more of the flexible segments. The flexible segments may include one or more of solid, hollow, and layered segments, in which the outer wall and/or the segments as a whole elastically flex upon the application of force. This flexibility facilitates use in applications such as deployment via human tissue that is susceptible to damage, such as for cardiac implementation. A tendon extends within the flexible segments and is coupled to manipulate one or more of the segments (e.g., for relatively large-scale movement), while the rigid actuators actuate and move one of the flexible segments to which it is connected (e.g., for relatively fine-scale movement). The tendon extends through some or all of the segments and, in some instances, through one or more of the rigid actuators, and passes within or through an outer segment wall. In some implementations, the apparatus includes a tool at the distal segment, such as for interacting with tissue upon deployment/engagement as controlled via positioning of the distal segment and/or a rigid actuator (e.g., that actuates the tool directly, or that actuates the distal segment).

In some embodiments, the apparatus also includes a manipulator that operates to position one or more of the segments by actuating the actuator using, for example, one or more of electrical, mechanical and electromagnetic input. In one such mechanical implementation, the manipulator includes a mechanical shaft that is connected between the manipulator and actuator, passing in one or more of the flexible segments. In such an electrical implementation, the manipulator includes an electrical link that is connected to one or more of the actuators and that passes an electrical input that controls the actuator. With regard to such an electrical input, various embodiments are directed to the implementation of actuators having components responsive to the electrical input, such as an electric motor that drives a mechanical component of the actuator, or a piezoelectric component that effects piezoelectric movement.

The rigid actuators operate to move the flexible segments in one or more of a variety of manners. In some embodiments, one or more of the rigid actuators include a mechanical joint that is responsive to an input received via the proximal segment, and moves one of the two flexible segments independently from movement of the other one of the two flexible segments. Such an input may be a mechanical input, such as received via a shaft and gear that interacts with a gear in the mechanical joint. Such an input may include an electrical input, with an electrical actuator being coupled to the mechanical joint.

The rigid actuators are controlled using one or more of a variety of approaches. In some embodiments, one or more of the actuators are moved using feedback indicative of a position of one of the segments. For instance, when feedback is indicative of motion errors in a segment, those motion errors can be detected (e.g., via position sensing) and used as feedback to fine-tune movement with one or more rigid actuators. Such an approach may be implemented, for example, with a rigid actuator that provides motion that overlaps with and/or is otherwise redundant with motion provided via a tendon, in which the rigid actuator corrects for motion carried out by the tendon.

The feedback may, for example, be provided using a feedback circuit that delivers a signal indicative of a position of a distal end of the apparatus, or of resistance to movement of the apparatus. Such a circuit may include, for example, a sensor coupled to one or more of the segments and the rigid actuators, and which senses positional or other characteristics of the distal segment and/or a tool deployed at the end of the distal segment.

Various other embodiments are directed to the implementation of one or more aspects as described in B. L. Conrad, J. Jung, R. S. Penning, and M. R. Zinn, "Interleaved Continuum-Rigid Manipulation An Augmented Approach For Robotic Minimally-Invasive Flexible Catheter-based Procedures," in *Robotics and Automation (ICRA), Proceedings IEEE International Conference on*, Karlsruhe, Germany (2013), which is fully incorporated herein by reference, as are the various references cited therein. Accordingly, various aspects as shown in this IEEE document and/or described in the references therein may be implemented in connection with one or more embodiments as described herein, such as by employing actuators, design approaches, and operational conditions amenable to implementation with these embodiments.

Turning now to the figures, FIG. 1 shows a manipulator apparatus 100 with interleaved flexible and rigid components, in accordance with another example embodiment. The apparatus 100 includes a plurality of flexible segments 110, 112, 114, 116 and 118 extending from a proximal end at 110 to a distal end at 112. Each segment has an outer wall that extends between respective ends of the segment. While several flexible segments are shown, various embodiments are directed to implementation with fewer (e.g., two) or greater (e.g., in excess of 10) segments. The outer wall of each flexible segment and/or the segments as a whole elastically flex upon the application of force to the outer wall, such as upon insertion and passage through human tissue.

The apparatus 100 also includes rigid actuators 120, 122 and 124, each actuator being coupled between two of the flexible segments and operable to actuate and move the flexible segments relative to one another. While three actuators are shown by way of example, various embodiments are directed toward the implementation of fewer (e.g., one) or more (e.g., 10 or more) actuators, to suit the particular application. These actuators may include, for example, an actuator at an end of a distal flexible segment, such as for positioning a tool or interaction with tissue, such as for delivering fluid.

The apparatus also includes one or more tendons 130 and a control input 132 for respectively controlling movement of the flexible segments. Tendon 130 extends within the flexible segments and is operable to manipulate one or more of the segments by moving in response to movement of the tendon at the proximal end (e.g., with the tendon sliding within the flexible segments via movement of a portion of the tendon extending out of the proximal end). For instance, such a tendon may extend to a portion and/or end of distal segment 112. Additional tendons are implemented in accordance with various embodiments, with the tendons used to control different movement characteristics of the apparatus such as via coupling to one or more of the flexible segments.

Rigid-link actuation control input 132 is coupled to the rigid-link actuators, and may be implemented using one more of a variety of control types. In one implementation, 132 is an electrical conductor that carries an electrical input that controls one or more of the rigid actuators 120, 122 and 124 for positioning one or more of the flexible segments. In another implementation, 132 is a mechanical shaft that is driven remotely and used to provide a mechanical input to one or more of the actuators 120, 122 and 124, to position one or more of the flexible segments.

In various embodiments, the apparatus includes a manipulator circuit (actuation controller) 140, which is coupled to the apparatus 100 via the proximal end 110. The manipulator positions at least one of the segments coupled to one of the actuators by generating and controlling the actuator using an electrical and/or mechanical control input via 132. The actuation controller circuit 140 may also, for example, be implemented to manipulate the flexible segments by controlling movement of the tendon 130.

In some embodiments, the actuation controller circuit 140 uses a feedback input 150 to control the rigid actuators. The feedback input 150 may, for example, be provided by an external feedback circuit that detects positioning characteristics of the segments. Other feedback input approaches involve obtaining feedback from the control 132, such as by sensing resistance to movement.

Figure 2:
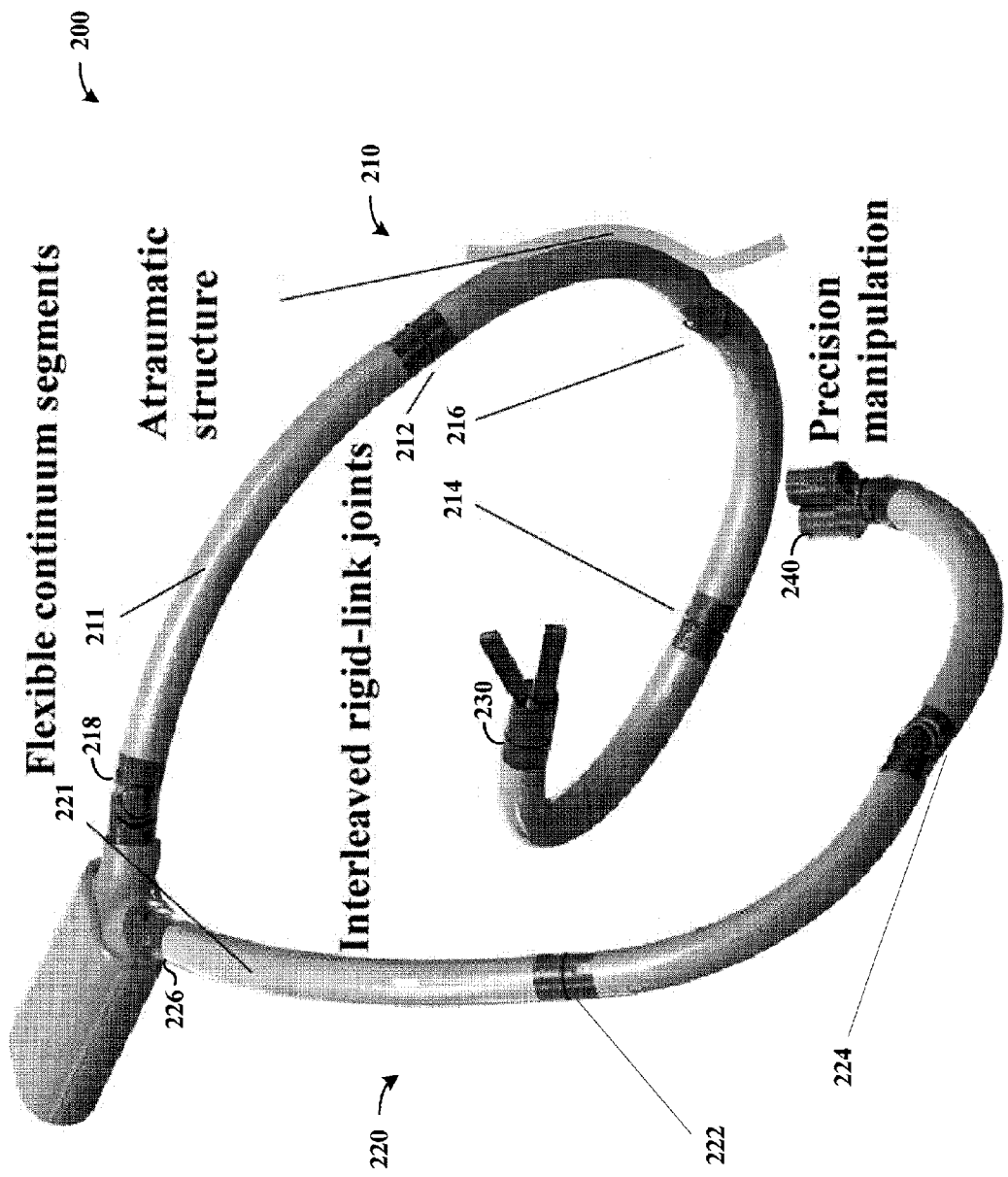
FIG. 2 shows another manipulator apparatus, with two distal ends having interleaved flexible and rigid components, in accordance with another example embodiment.

FIG. 2 shows another manipulator apparatus 200, with two interleaved manipulators 210 and 220 each having both flexible and rigid components, in accordance with another example embodiment. Referring to manipulator 210, flexible segments including segment 211 are joined by respective rigid actuators 212, 214, 216 and 218, with a tool 230 coupled to the end of a distal segment. Manipulator 220 is similar to manipulator 210, with flexible segments including segment 221 being joined by rigid actuators 222, 224 and 226, and with a tool 240 coupled at an end of a distal segment. The respective rigid actuators may be implemented with different diameters to suit particular applications.

Figure 3:
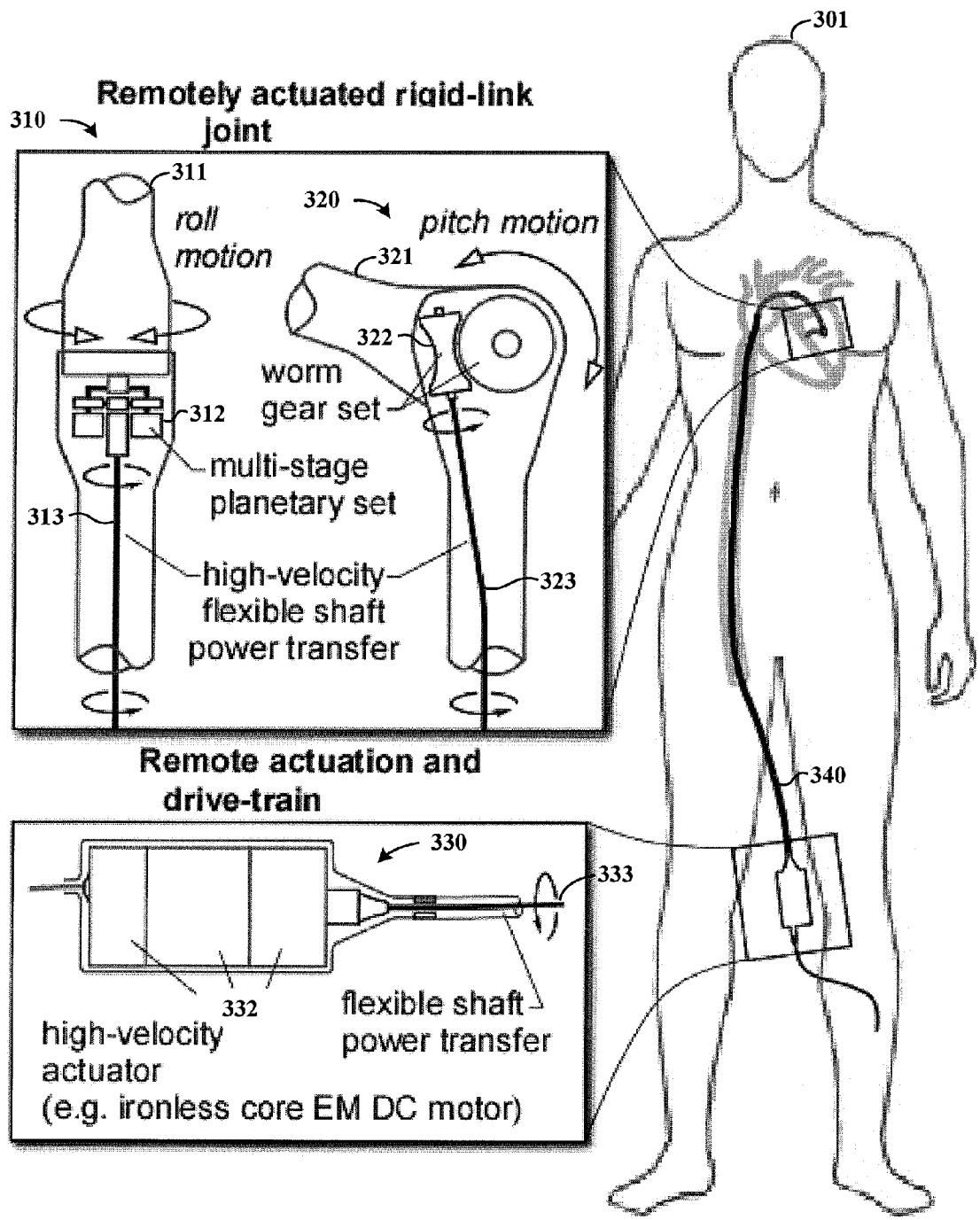
FIG. 3 shows rigid actuators and a shaft-driven control, in accordance with other example embodiments.

FIG. 3 shows rigid actuators 310 and 320, with a shaft-driving controller 330, in accordance with other example embodiments. The rigid actuators 310 and 320 and the controller 330 may, for example, be implemented in connection with the apparatuses shown in FIGS. 1 and 2, for use in a human patient 301. Rigid actuator 310 includes a multi-stage planetary gear set 312 driven by a flexible shaft 313, for roll actuation of portion 311 (e.g., a flexible segment as discussed herein, or a connector that is connected to such a flexible segment). Rigid actuator 320 includes a worm gear set 322 driven by a shaft 323 for pitch motion as shown with portion 321 (similar to 311). In some embodiments, a dual-stage worm gear set is used for higher reduction.

The shaft-driving controller 330 includes a motor/actuator 332 such as an electromagnetic motor, which is coupled to shaft 333 (e.g., directly or via a gear) to impart motion thereto. Shaft 333 may be connected to shaft 313 or 323, for particular implementations. When implemented, the shaft 333 is extended into a flexible manipulator 340, which can be implemented for intravascular, minimally-invasive surgery in patient 301. A distal end region of the flexible manipulator is shown by way of example extending into the patient's heart. The controller 330 is implemented to control pitch and/or roll of one or more rigid-link actuators, for positioning the manipulator. In some implementations, a high reduction gear is located at the driven joint in rigid actuators 310, 320, and increases an output reflected stiffness by $N^2$, N representing a gear ratio or equivalently the ratio of flexible shaft velocity to driven joint velocity. The increase in stiffness can be used to enhance disturbance rejection characteristics and reduce the effect of disturbances on actuator control.

The interleaved manipulator approaches described herein facilitate performance and dexterity in a variety of manners. In some implementations, flexible segment control tendons are routed along a center line of proximal flexible segments, such that tendon tensions do not induce significant curvature in proximal segments (e.g., as applicable for implementation with patient 301). In addition, control tendons can be routed through the rotation axis of proximal rigid-links such that tendon lengths do not change as a result of rigid joint motion, resulting in little to no net work done and thus limited or no cross-motion coupling. Decoupling the motions can facilitate the overall control approach as well as minimize actuation requirements for both the flexible and rigid-link actuators. Coupled-designs are also implemented for certain embodiments.

Figure 4:
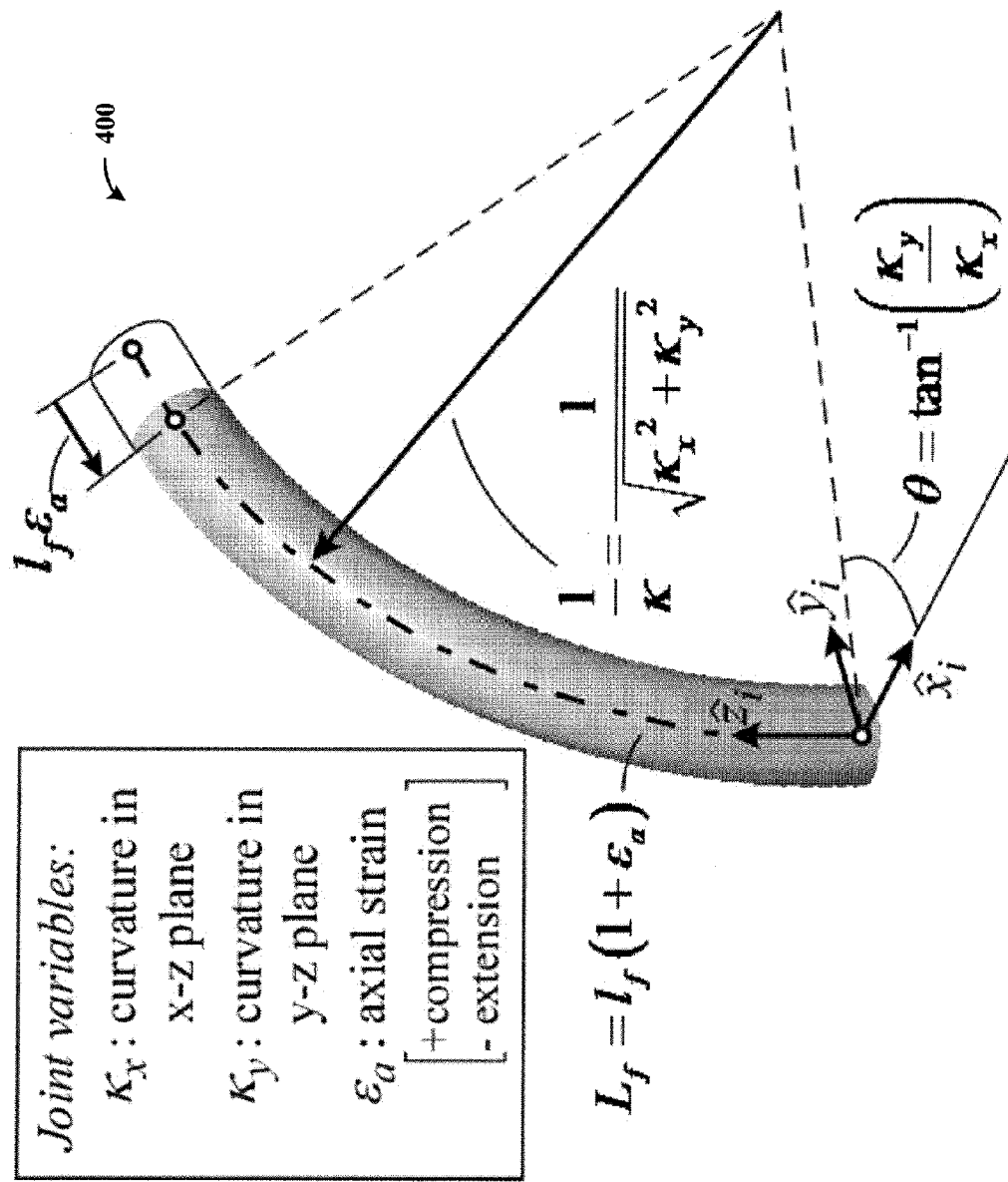
FIG. 4 shows a portion of a flexible segment, in accordance with another example embodiment.

A variety of different types of flexible segments can be implemented to suit particular embodiments. FIG. 4 shows a portion of one such flexible segment 400, in accordance with another example embodiment. Flexible segment motions, or joint variables, are represented by the segment curvatures, $\kappa_x$ and $\kappa_y$, representing the curvature in the x-z and y-z planes respectively, and the axial strain, $\epsilon_a$. Assuming a consistent application of control tendon tension, these three joint variables are not independent. By way of example, it can be assumed that curvatures, $\kappa_x$ and $\kappa_y$ are independently specified while the axial strain, $\epsilon_a$ is a dependent variable. This approach assumes that the articulation of the flexible segment results in constant curvature over the complete length of the segment. For this assumption to hold, the effects of internal control tendon friction are implemented such that they are negligible, as significant friction would cause the segment curvature to vary as a function of control tendon motion.

The kinematics of a single flexible segment can be represented using a homogeneous transformation, $T_f$, where the elements of $T_f$ are a function of the joint variables $\kappa_x$, $\kappa_y$ and $\epsilon_a$. Such kinematics may be implemented in accordance with the approaches describing the homogeneous transformation $T_f$ and using these variables further below, and in connection with experimental-type embodiments.

The rigid-link kinematics are a function of the specific joint mechanism design. By way of example, rigid joint kinematics is represented by a homogeneous transformation, $T_r$. The forward kinematics of the complete manipulator are assembled via the chain rule. When the flexible and rigid-link degrees-of-freedom are successively alternated, the complete manipulator forward kinematics are given as:

$$T = \prod_{i=1}^{n} (T_r)_i (T_f)_i.$$

In this case, the rigid joint is assumed to be proximal to the corresponding flexible segment. In addition to the forward kinematics, a control approach as discussed herein can be implemented based on instantaneous kinematics of the manipulator, which uses a Jacobian relating the flexible segment and rigid-link joint velocities to task space velocities. The Jacobian J can be formed numerically and evaluated using the forward kinematics, where the elements of J are the partial derivatives of task motions with respect to joint motions. The task-space Jacobian is represented by J and is partitioned between flexible segment and rigid-link motions:

$$J = [J_f | J_r]$$

Figure 5:
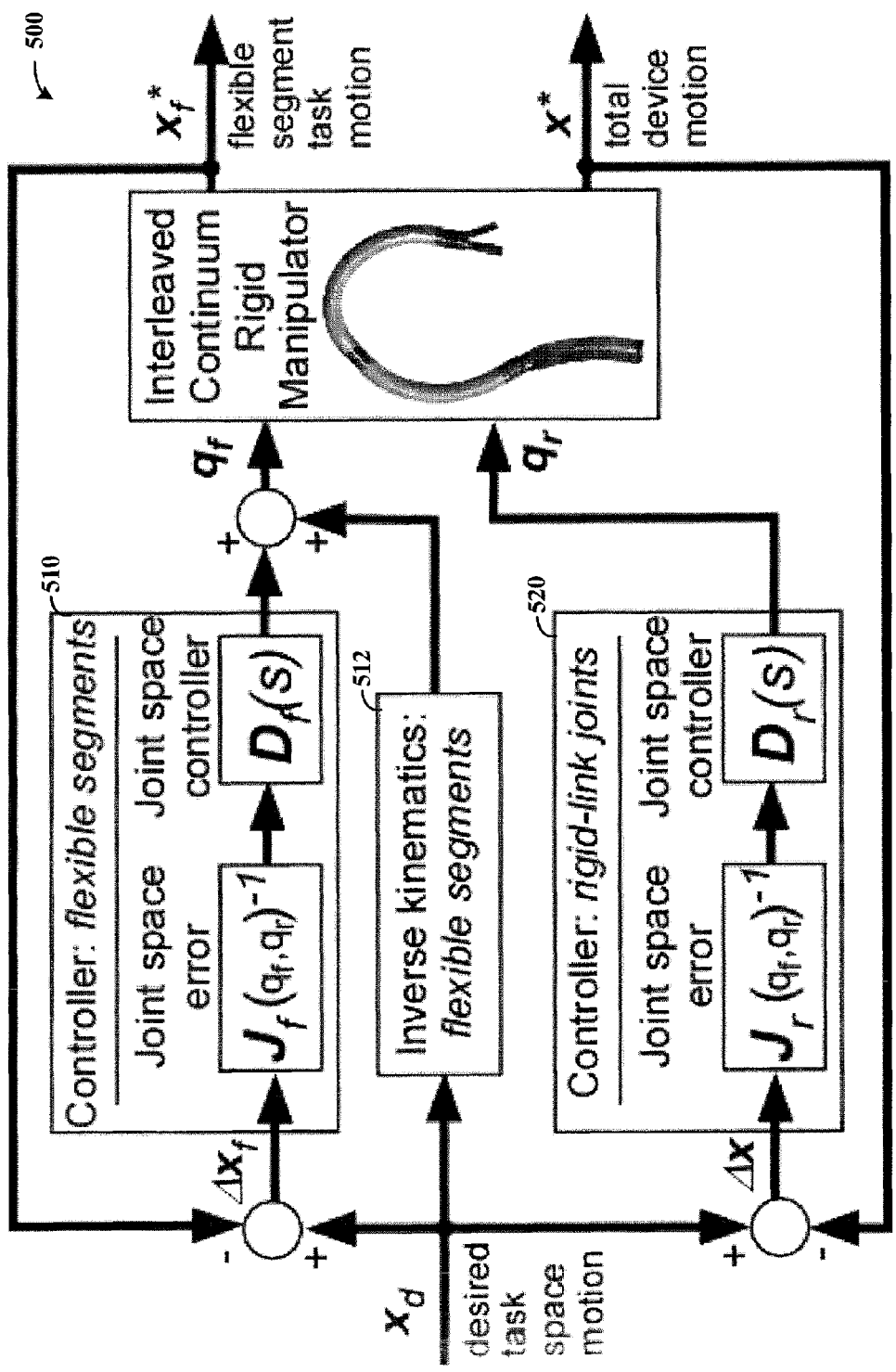
FIG. 5 shows a controller and control approach for controlling a manipulator apparatus, in accordance with another example embodiment.

FIG. 5 shows a controller 500 and control approach for controlling a manipulator apparatus such as shown in FIGS. 1 and 2, in accordance with another example embodiment. Blocks 510 and 520 respectively implement flexible segment and rigid-link joint control, with block 512 implementing feed-forward inverse kinematics to sum with the output of block 510. The flexible segment controller block 510 acts on an error between a task space motion command, $x_d$, and a measured motion of the flexible segment, $x_f^*$. This approach can be implemented to limit the motion of limited-stroke rigid-link joints while correcting for motion errors that result from flexible segments. The flexible segment task motion, $x_f^*$, is formed by subtracting the motion attributable to the rigid-link joint motion, $x_r^*$, from the measured total device motion, $x^*$.

The feed-forward inverse kinematics block 510 converts the desired task space configuration to flexible segment joint commands (e.g., segment curvatures). The inverse kinematics pertaining to the coupled motion of the flexible sections (exclusive of rigid-link joint motion) can be obtained using a multivariable Newton's method. The Jacobian, $J_f$, relating flexible segment joint velocities to the task-space velocities is used in an iterative solver. The controller, which acts on the error associated with the flexible segment alone, transforms the task space error to equivalent joint space (of the flexible segments) via the flexible segment Jacobian, $J_f$. The joint space error is fed through a compensation block, $D_f(s)$, whose output is summed with the feed-forward term to produce the flexible segment joint space position command, $q_f$. The rigid-link joint controller acts on the error defined as the difference between the desired task space motion command, $x_d$, and the total measured device motion, $x^*$. This error is transformed from task space to the rigid-link joint space via the rigid-link joint Jacobian, $J_r$. This joint space error is then fed through a compensation block, $D_r(s)$ to produce the rigid-link joint space position command, $q_r$.

Figure 6:
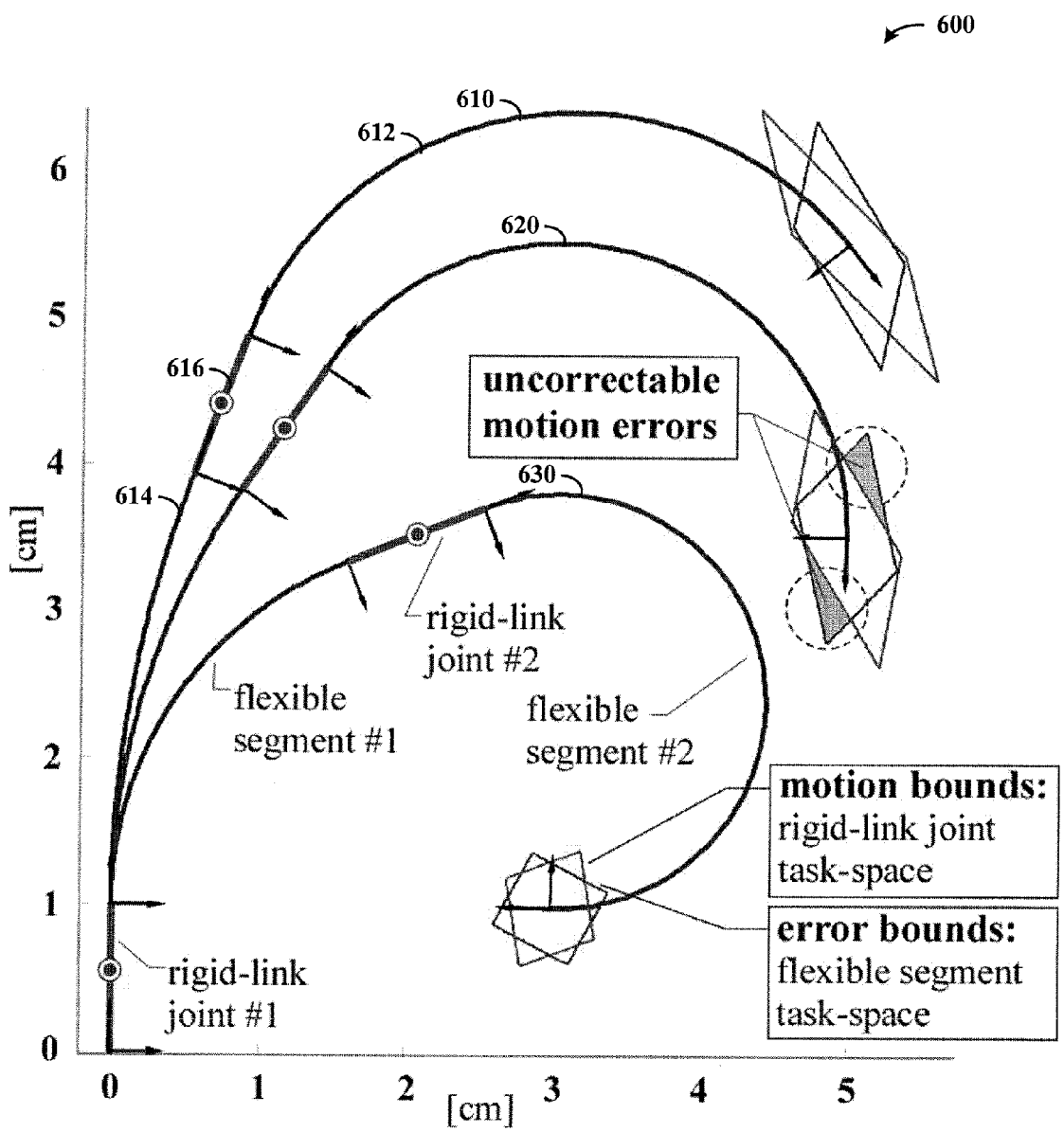
FIG. 6 shows a manipulator at different positions and related control aspects, as may be implemented in accordance with one or more embodiments.

FIG. 6 shows a manipulator apparatus 600 at different positions 610, 620 and 630, as may be implemented in accordance with one or more embodiments. Using position 610 by way of example, two flexible segments 612 and 614 are coupled by a rigid-link actuator 616. Both the flexible segment Jacobian, $J_f$, and rigid-link joint Jacobian, $J_r$, are functions of the manipulator's configuration. The proximal and distal flexible segment articulation errors depicted are ±0.10 radian and ±0.15 radian, respectively. The rigid-link joint range of motion depicted is ±0.10 radian. In some implementations, task space motion bounds of the rigid-link joints envelope the task-space error bounds of the flexible segments for certain motion. Exemplary regions of uncorrectable error are depicted for position 620, and are a function of the range of motion of the rigid-link joints, which can be effected as a trade-off between joint size and desired motion.

Figure 7:
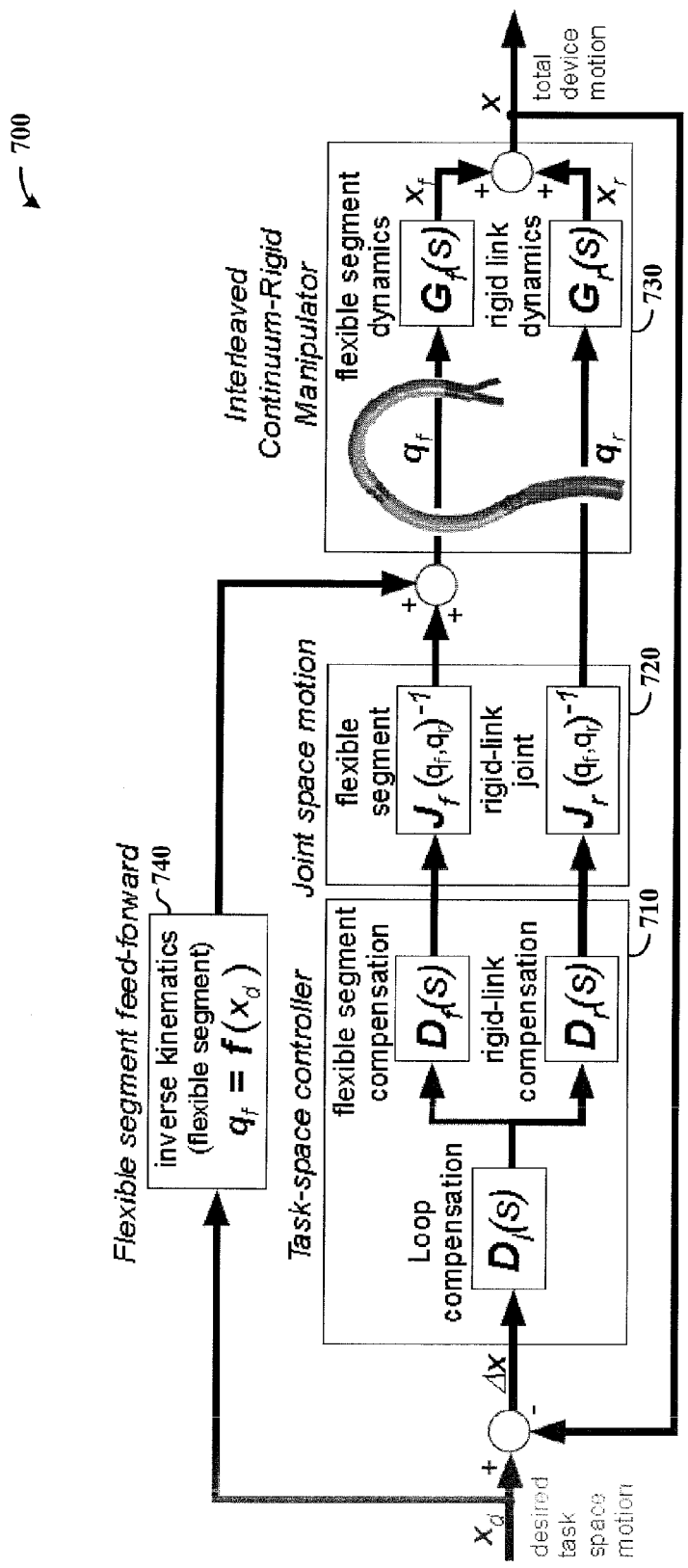
FIG. 7 shows a controller and control approach for controlling a manipulator apparatus, in accordance with another example embodiment.

FIG. 7 shows a controller and control approach 700 for controlling a manipulator apparatus such as shown in FIGS. 1 and 2, in accordance with another example embodiment. A task-space control signal is transformed to joint space motion commands at blocks 710 and 720 using the flexible and rigid space Jacobians $J_f$ and $J_r$, which can be tailored to the particular manipulator with which the controller is used, as represented at block 730 with flexible segment and rigid link dynamics indicative of total device motion. While the specific structure of the compensation blocks ($D_f(s)$, $D_r(s)$, and $D_i(s)$) can vary depending on the specific dynamics of the system under consideration and the desired performance goals, there are general considerations for both the flexible segment and rigid-link control that are implemented for the compensator design to suit particular embodiments. For instance, some embodiments are directed to robotic catheter systems that regulate control tendon motion with a high-gain position controller that acts on the control tendon actuator positions. This can be implemented to improve disturbance rejection by increasing the static stiffness at the control tendon output, and to improve stability margins. In addition, local joint controllers can be implemented with relatively fast closed-loop dynamics, for use in cardiac interventional catheters, with control inputs to the interleaved manipulator being given in terms of joint displacements (qf and qr).

The following discussion depicts various embodiments and experimental-type applications, as may be implemented in connection with each other and/or embodiments discussed or shown elsewhere herein. Various such aspects are thus directed to a manipulator having flexible segments and interleaved rigid-links coupling flexible segments together.

In some embodiments, a two degree-of-freedom planar manipulator simulation is used to explore effects of dynamic coupling and internal friction in a flexible segment as discussed herein. This approach facilitates development of control approaches for multiple degree of freedom manipulators. Flexible segments are modeled by a serial chain of links constrained by revolute joints. Flexible segment bending compliance and internal damping are modeled with parallel springs and dampers which act across the revolute joint. Flexible segment control inputs, applied via control tendon tension, are applied as torques at the revolute joints where the tension magnitude and local curvature determine the magnitude of the applied torques. A modified Dahl friction model is used to model the effects of internal control tendon friction, which can have a significant effect on flexible segment motion, where the steady-state Dahl friction torque is related to control tendon tension as well as local flexible segment curvature. For simplicity, the modified Dahl friction torques can be applied directly at the joints, as opposed to applying forces at the tendon sliding interface.

The rigid-link joints are modeled as revolute joints which can impose a displacement between successive flexible segments. This can be carried out using an assumption that the rigid-link joints have output impedance that is sufficiently high such that the dynamics of the flexible segments have negligible effect on their relative position. In addition, the simulation may be implemented with an assumption that the rigid-links are designed such that the flexible segment control tendon tension and rigid-link joint motion are uncoupled. This uncoupling can be achieved by routing the control tendons across the rigid-link joints such that joint motion does not result in a control tendon length change (and thus resulting in no work being done).

Example control structure implemented in the simulation is described below. Task space motion is defined as the planar position of the tip of the manipulator. In this case, the flexible and rigid-link compensations, $D_f(s)$ and $D_r(s)$, include integral controllers, as relative to open-loop uncompensated system dynamics. At frequencies below the first flexible mode of the manipulator, the task space motion, in this case planar tip translation, is related to the input joint motions (e.g., flexible segment curvature and rigid-link rotations) by a gain, with no phase distortion. The integral controller achieves a cross-over frequency below the first mode frequency, while maintaining sufficient gain margin. Use of alternative compensation approaches may be directed or limited by the manipulator's flexible modes. For example, control action can be implemented to mitigate cross-over frequency above a frequency of the first flexible mode, and therein enhance stability.

The planar simulation described above can be used to evaluate the performance of an interleaved continuum-rigid manipulation approach and compare it to flexible segment manipulator control. The flexible segment manipulator is controlled using the same control structure as the interleaved system, absent the rigid-link motion and control. The controller gains are adjusted upward until signs of instability were observed. As a baseline, both approaches are compared to a flexible segment manipulator without feedback control.

In a particular experimental-type embodiment, a manipulator is positioned approximately in the center of its workspace. A small motion (e.g., 5 mm) step input command is applied and the position control performance is simulated. The uncompensated flexible segment manipulator response exhibits a time constant of approximately 0.5 seconds with a steady-state error of 0.6 mm, which may be a result of the internal control tendon friction. A flexible segment manipulator is implemented with closed-loop control, which is used to mitigate or eliminate the steady-state error. The response of the interleaved manipulator under closed-loop control shows significant improvement as compared to the flexible segment manipulator. Both the speed of the initial response, as well as the speed in which the error is driven to zero, are improved. In this case, the time constant of the interleaved system is approximately one third that of the closed-loop flexible segment manipulator.

In another experimental-type embodiment, a manipulator is commanded along a circular trajectory of 20 mm radius. The tracking time to complete one revolution is 32 seconds. The trajectory tracking results demonstrate that an uncompensated flexible segment manipulator exhibits significant tracking error, due to the effects of internal control tendon friction that distort the deflection of the flexible segments. In the case of the flexible segment manipulator with closed-loop control, the tracking response shows improvement as compared to the uncompensated flexible segment manipulator. The speed of the controller can be increased to compensate for the change in friction due to the moving internal control tendons. The tracking response of the interleaved manipulator under closed-loop control shows almost an order of magnitude reduction in position error as compared to the flexible segment manipulator.

In some embodiments, rigid-link joint motion is used to provide rotation about a pivot axis located at the base of a flexible segment. Flexible segment control tendons are routed through a rotation axis of the rigid-link to eliminate coupling between the flexible and rigid-link motions. The rigid-link joints are actuated via a voice-coil actuator through a slider-crank mechanism. Task space motion is defined as a horizontal position of a catheter tip. As above, the flexible and rigid-link compensation, $D_f(s)$ and $D_r(s)$, are implemented with integral controllers. Catheter tip motion is acquired with an Ascension trakStar 3D magnetic position sensor, operating at 20 Hz, providing a globally-referenced measurement of the catheter's tip position. The controller and sensor input is implemented using Matlab xPC 2009a.

The kinematics of a single flexible segment as described herein can be represented using a homogeneous transformation, $T_f$, as follows:

$$T_f = \left[\begin{array}{c|c} R_f & \vec{P}_f \\ \hline 0\,0\,0 & 1 \end{array}\right]$$

The rotation matrix, $R_f$, can be evaluated using the axis-angle representation [23] for a rotation, $\alpha$, about a fixed axis, $\hat{k}$:

$$R_f = \begin{bmatrix} k_x^2 v_\alpha + c_\alpha & k_x k_y v_\alpha - k_z s_\alpha & k_x k_z v_\alpha + k_y s_\alpha \\ k_x k_y v_\alpha + k_z s_\alpha & k_y^2 v_\alpha + c_\alpha & k_y k_z v_\alpha - k_x s_\alpha \\ k_x k_z v_\alpha - k_y s_\alpha & k_y k_z v_\alpha + k_x s_\alpha & k_z^2 v_\alpha + c_\alpha \end{bmatrix},$$

where $c_\alpha = \cos\alpha, s_\alpha = \sin\alpha, v_\alpha = 1 - \cos\alpha,$ and the rotation magnitude, $\alpha$, is given as $\alpha = \kappa L_f.$ The length of the flexible segment, $L_f$, and the total curvature, $\kappa$, are given as:

$$L_f = l_f(1 + \varepsilon_\alpha)$$

$$\kappa = \sqrt{\kappa_x^2 + \kappa_y^2},$$

in which $l_f$ is the non-deformed length of the flexible segment. The unit vector about which the rotation occurs is given as:

$\hat{k} = [k_x\ k_y\ k_z]^T = [\sin\theta\ \cos\theta\ 0]^T,$ where roll angle, $\theta$, is evaluated by:

$\theta = \tan^{-1}(\kappa_y/\kappa_x).$

The position vector, $\vec{P}_f$, is given as:

$$\vec{p_f} = \begin{bmatrix} x_f \\ y_f \\ z_f \end{bmatrix} = \frac{1}{\kappa} \begin{bmatrix} (1 - \cos\alpha)\cos\theta \\ (1 - \cos\alpha)\sin\theta \\ \sin\alpha \end{bmatrix}.$$

The interleaved approach can be used to compensate for flexible segment motion errors when these errors cannot be addressed through closed-loop flexible segment control alone. These approaches can be used to address issues such as those discussed in the background above, in which significant nonlinear, non-stationary behavior is observed, and in which closed-loop control can break down such as with multi-degree of freedom catheter devices. For instance, where bi-planar catheter articulation and telescoping motion (from a supporting sheath) are desired, an interleaved approach can be used to mitigate or avoid significant frictional forces, as may occur between control tendons and control lumens, and between telescoping segments.

As consistent with one or more embodiments herein, actuation control may be effected using a variety of types of circuitry and circuit-based controllers (e.g., processors programmed to process and implement feedback to effect the mechanical control of an actuator). Accordingly, various blocks, modules or other circuits may be implemented to carry out one or more of the operations and activities described herein and/or shown in the figures. In these contexts, a "block" (also sometimes "logic circuitry" or "module") is a circuit that carries out one or more of these or related operations/activities (e.g., controlling actuation of a rigid-link joint, or processing a feedback signal to operate a rigid-link joint). For example, in certain of the above-discussed embodiments, one or more modules are discrete logic circuits or programmable logic circuits configured and arranged for implementing these operations/activities, as in the circuit module 140 shown in FIG. 1. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions. Certain embodiments are directed to a computer program product (e.g., nonvolatile memory device), which includes a machine or computer-readable medium having stored thereon instructions which may be executed by a computer (or other electronic device) to perform these operations/activities.

Based upon the above discussion and illustrations, those skilled in the art will readily recognize that various modifications and changes may be made to the various embodiments without strictly following the exemplary embodiments and applications illustrated and described herein. For example, different types of rigid-link actuators are implemented to suit certain applications, such as to provide dexterity and/or to compensate for flexible segment motion errors. Such modifications do not depart from the true spirit and scope of various aspects of the disclosure, including aspects set forth in the claims.

What is claimed is:

1. An apparatus comprising:
    a plurality of flexible segments, each segment having an outer wall that extends between respective ends of the segment, the outer wall being configured and arranged to elastically flex upon the application of force to the outer wall, the segments being coupled end-to-end and including at least a proximal segment and a distal segment;
    at least one rigid actuator coupled between two of the flexible segments and configured and arranged to actuate and move one of the two flexible segments relative to the other one of the two flexible segments;
    a tendon extending within the flexible segments, the tendon being coupled to the distal segment and configured and arranged to manipulate the distal segment by moving in response to movement of the tendon at the proximal segment; and
    a manipulator circuit coupled to at least a first one of the actuators and configured and arranged to position at least one of the segments coupled to the first actuator by actuating the first actuator.

2. The apparatus of claim 1, further including a mechanical shaft connected between the manipulator circuit and the first actuator, the mechanical shaft passing within the outer wall of at least one segment located between the first actuator and the manipulator circuit, the manipulator circuit being configured and arranged to actuate the first actuator via the mechanical shaft.

3. The apparatus of claim 1,
    further including an electrical link connected between the manipulator circuit and the first actuator, the electrical link passing within the outer wall of at least one segment located between the first actuator and the manipulator circuit, and
    wherein the manipulator circuit is configured and arranged to electrically actuate the first actuator by passing an electrical control output via the electrical link.

4. The apparatus of claim 3, wherein the at least one actuator includes an electric motor configured and arranged to drive a mechanical component of the first actuator in response to the electrical control output.

5. The apparatus of claim 1, wherein each actuator includes a rigid mechanical joint that is responsive to an input received via the proximal segment and is configured and arranged to move one of the two flexible segments independently from movement of the other one of the two flexible segments.

6. The apparatus of claim 1, wherein the manipulator circuit is configured and arranged to actuate the first actuator in response to feedback indicative of a position of one of the segments.

7. The apparatus of claim 6, wherein the feedback is indicative of motion errors in at least one of the flexible segments.

8. The apparatus of claim 6, wherein the first actuator is configured and arranged to compensate for motion errors effected via the tendon by moving the one of the flexible segments in a manner that is redundant with manipulation of the one of the flexible segments provided via the tendon.

9. The apparatus of claim 6, further including a feedback circuit configured and arranged to provide the feedback to the manipulator circuit as a feedback signal.

10. The apparatus of claim 9, further including a sensor coupled to at least one of the segments and the rigid actuators and configured and arranged to sense a positional characteristic of the distal segment and to provide an output indicative of the sensed positional characteristic, the feedback circuit being configured and arranged to couple the output from the sensor to the manipulator circuit as the feedback signal.

11. The apparatus of claim 1, further including a tool coupled to the distal segment, the apparatus being configured and arranged to deploy and interact with tissue via the tool, and wherein the manipulator circuit is configured and arranged to position the tool by actuating the first actuator.

12. The apparatus of claim 11, further including a rigid actuator coupled between the tool and the distal segment and configured and arranged to manipulate the tool relative to the distal segment.

13. The apparatus of claim 1, further including at least one additional segment coupled between the proximal and distal segments, the tendon extending to the distal segment via the at least one additional segment and being coupled to an end of the distal segment.

14. A surgical apparatus comprising:
    a plurality of elongated segments coupled end-to-end, the segments including at least a first segment and a second segment, each segment being configured and arranged to elastically flex upon contact with tissue of a patient during insertion of the segment into the tissue;
    a rigid actuator coupled between the first and second segments and configured and arranged to actuate and move the first segment relative to the second segment;
    a tendon extending through a proximal one of the segments and configured and arranged to manipulate at least one of the segments in response to movement of the tendon at the proximal segment; and
    a tool at a distal one of the segments and configured and arranged to facilitate interaction with the tissue via the distal segment, in response to movement of the rigid actuator and the tendon.

15. The apparatus of claim 14, further including an actuator circuit electrically coupled to the rigid actuator and configured and arranged to actuate and move the first segment relative to the second segment by controlling movement of the rigid actuator.

16. The apparatus of claim 15,
    further including a feedback circuit configured and arranged to generate a feedback signal indicative of a position of one of the plurality of segments, and wherein the actuator circuit is configured and arranged to control movement of the rigid actuator in response to the feedback signal.

17. The apparatus of claim 15, wherein the actuator circuit includes an electric motor connected to a mechanical component of the rigid actuator and configured and arranged to drive the mechanical component in response to an electrical control output.

18. The apparatus of claim 14, wherein the ridged rigid actuator includes mechanical linkage connected to each of the first and second segments and being configured and arranged to move the first segment relative to the second segment in response to a mechanical input.

19. A surgical method comprising:
   inserting a manipulator into tissue of a patient, the manipulator including plurality of flexible segments, at least one rigid actuator coupled between two of the flexible segments and a tendon extending within the flexible segments, each segment having an outer wall that extends between respective ends of the segment, the outer wall being configured and arranged to elastically flex upon the application of force to the outer wall via insertion into the tissue, the segments being coupled end-to-end and including at least a proximal segment and a distal segment; and
   positioning the distal segment by moving the tendon via the proximal segment and controlling the rigid actuator to actuate and move one of the two flexible segments relative to the other one of the two flexible segments.

20. The method of claim 19, wherein controlling the rigid actuator to actuate and move one of the two flexible segments relative to the other one of the two flexible segments includes controlling the rigid actuator in response to feedback indicative of a positional characteristic of the distal segment, further including using a manipulator circuit to control the rigid actuator to move the one of the two flexible segments relative to the other one of the two flexible segments.

* * * * *